(12) United States Patent
Baumfalk et al.

(10) Patent No.: US 10,281,319 B2
(45) Date of Patent: May 7, 2019

(54) DOSING DEVICE WITH INTEGRATED BALANCE AND CLIMATE MODULE

(71) Applicant: Sartorius Lab Instruments GmbH & Co. KG, Goettingen (DE)

(72) Inventors: Reinhard Baumfalk, Goettingen (DE); Rainer Kirchhoff, Hattorf (DE); Jean-Claude Bertoldi, Goettingen (DE)

(73) Assignee: SARTORIUS LAB INSTRUMENTS GMBH & CO. KG, Goettingen (DE)

( * ) Notice: Subject to any disclaimer, the term of this patent is extended or adjusted under 35 U.S.C. 154(b) by 162 days.

(21) Appl. No.: 15/149,909

(22) Filed: May 9, 2016

(65) Prior Publication Data
US 2016/0252386 A1    Sep. 1, 2016

Related U.S. Application Data

(63) Continuation of application No. PCT/EP2014/002854, filed on Oct. 22, 2014.

(30) Foreign Application Priority Data

Nov. 8, 2013    (DE) .................. 10 2013 018 767
Feb. 7, 2014    (DE) .................. 10 2014 101 561

(51) Int. Cl.
*G01G 23/48*      (2006.01)
*G01G 23/01*      (2006.01)
(Continued)

(52) U.S. Cl.
CPC .............. *G01G 23/01* (2013.01); *B01L 3/021* (2013.01); *G01G 17/04* (2013.01); *G01G 19/303* (2013.01);
(Continued)

(58) Field of Classification Search
CPC ........ G01G 23/01; G01G 23/48; G01G 17/04; G01G 19/303; G01G 21/22; G01G 21/286; B01L 3/021; G01N 9/26; G05D 11/00
See application file for complete search history.

(56) References Cited

U.S. PATENT DOCUMENTS 4,656,599 A * 4/1987 Knothe ..................... G01G 7/02
                                                                   177/212
4,858,161 A * 8/1989 Baumann ............... G01G 23/01
                                                                   702/101
(Continued)

FOREIGN PATENT DOCUMENTS

DE        4407433 C2    12/1995
DE       29912867 U1    3/2000
(Continued)

OTHER PUBLICATIONS

International Search Report in counterpart International Application No. PCT/EP2014/002854, dated Dec. 4, 2014.
(Continued)

*Primary Examiner* — Natalie Huls
(74) *Attorney, Agent, or Firm* — Edell, Shapiro & Finnan, LLC

(57) ABSTRACT

A dosing device with a balance, which includes a weighing chamber (16); a processor (32); a climate module (34), which is disposed in the weighing chamber (16); a data transmission path, over which data is exchanged between the climate module (34) and the processor (32); and a mixing formulation display (30). Also disclosed are a climate module configured to electrically couple to a dosing device in a detachable manner, wherein the climate module (34) forms a self-contained modular unit and includes various sensors (52, 54, 62) and a path over which data is transmitted to a processor external to the climate module, and a method for
(Continued)

mixing a formulation, using a dosing device, wherein ambient conditions are detected during dosage of the substances to be combined, and the mixing ratio is adjusted in accordance with the detected ambient conditions.

13 Claims, 3 Drawing Sheets

(51) Int. Cl.
G01G 17/04 (2006.01)
G01G 21/28 (2006.01)
B01L 3/02 (2006.01)
G01G 19/30 (2006.01)
G05D 11/00 (2006.01)
G01G 21/22 (2006.01)
G01N 9/26 (2006.01)

(52) U.S. Cl.
CPC ........... G01G 21/22 (2013.01); G01G 21/286 (2013.01); G01G 23/48 (2013.01); G01N 9/26 (2013.01); G05D 11/00 (2013.01)

(56) References Cited

U.S. PATENT DOCUMENTS

| | | | |
|---|---|---|---|
| 5,847,328 A | 12/1998 | Oldendorf et al. | |
| 6,615,638 B1* | 9/2003 | Lochner | B01L 3/021 177/1 |
| 8,285,497 B2* | 10/2012 | Bachmann | G01G 17/06 702/101 |
| 9,354,109 B2* | 5/2016 | Izumo | G01G 23/01 |
| 9,752,923 B2* | 9/2017 | Izumo | G01G 23/42 |
| 2003/0221874 A1* | 12/2003 | Leisinger | G01G 21/286 177/180 |
| 2007/0006942 A1* | 1/2007 | Pluvinage | B01L 3/021 141/83 |
| 2007/0119226 A1* | 5/2007 | Tellenbach | G01G 21/30 73/1.15 |
| 2008/0110681 A1* | 5/2008 | Von Arb | G01G 3/1414 177/25.13 |
| 2008/0173668 A1* | 7/2008 | Bloechlinger | G01F 13/00 222/1 |
| 2008/0257039 A1* | 10/2008 | Thiel | G01G 17/06 73/382 R |
| 2010/0100038 A1* | 4/2010 | Walker | A61M 5/14244 604/82 |
| 2010/0288566 A1* | 11/2010 | Luchinger | G01G 21/286 177/180 |
| 2010/0298957 A1* | 11/2010 | Sanchez Rocha | G05B 15/02 700/90 |
| 2014/0000390 A1* | 1/2014 | Laubstein | B01L 3/021 73/863.44 |
| 2014/0016432 A1* | 1/2014 | Lehtonen | G01G 11/086 366/138 |
| 2014/0297229 A1* | 10/2014 | Izumo | G01G 23/00 702/189 |
| 2016/0250628 A1* | 9/2016 | Graf | G01G 17/04 73/1.74 |

FOREIGN PATENT DOCUMENTS

EP 1975577 A1 10/2008
EP 2251657 A1 11/2010

OTHER PUBLICATIONS

International Preliminary Report on Patentability in counterpart International Application No. PCT/US2014/002854, dated May 12, 2016, 7 pages.

* cited by examiner

DOSING DEVICE WITH INTEGRATED BALANCE AND CLIMATE MODULE

CROSS REFERENCE TO RELATED APPLICATIONS

This is a Continuation of International Application PCT/EP2014/002854, which has an international filing date of Oct. 22, 2014, and the disclosure of which is incorporated in its entirety into the present Continuation by reference. The following disclosure is also based on and claims the benefit of and priority under 35 U.S.C. § 119(a) to German Patent Application Nos. DE 10 2013 018 767.2, filed Nov. 8, 2013, and to DE 10 2014 101 561.4, filed Feb. 7, 2014, which are also incorporated in their respective entireties into the present Continuation by reference.

FIELD OF THE INVENTION

The invention relates to a dosing device, with which liquid and/or solid substances can be combined in a defined mixing ratio, i.e., according to a defined formulation, with high accuracy.

BACKGROUND

Dosing tasks, according to a defined formulation of liquid and/or solid substances, are often performed on balances. In this context the formulations are usually generated from databases either statically (fixed formulation) or dynamically (formula-based formulation).

The European patent EP 1 975 577 A1 discloses a balance that is designed for the gravimetric calibration of pipettes and that has a draft shield and built-in temperature, air pressure and air humidity sensors.

The German patent DE 44 07 433 C2 discloses a balance for dosing. In the event of an incorrect dosage of the individual constituents this balance can be used to make a correction of the dosing of the rest of the constituents within a formulation. The drawback is that during dosage of the individual constituents, only the percentage by mass of the individual constituents is considered.

Even in the case of a dynamic formulation, however, the current ambient conditions (temperature, humidity, time, . . . ) are not considered at the location and time of the dosing process, so that the formulation may not meet the requirements of the subsequent application.

One example of this effect of the ambient conditions are mixtures of volatile constituents, the proportion of which varies in the subsequent processing steps, as a function of the evaporation rate, which prevails at the weighing location and which is largely determined by the air temperature and the air humidity. It affects, for example, liquid mixtures that contain alcohol. On the other hand, during dosage of hygroscopic substances as a constituent of a formulation, the effect of the climate parameters, for example, is important, in particular, the effect of the air temperature and the humidity.

Another example are mixtures having a viscosity that depends on the ambient temperature and in subsequent process steps should have a specified target value, for example, baking mixes with variable fat or water content. In this case it would be desirable for the formulation to be corrected according to the current and local ambient conditions, with the result that the viscosity value meets the requirements for the kneading or molding processes.

In addition, the ambient conditions in the subsequent processing steps affect the end results. For example, the ambient humidity affects paint mixtures that are sprayed, because the drying process and the curing process run at different speeds due to the ambient humidity. If in this case the objective is to achieve the same application quality, irrespective of the ambient humidity, then a suitably adjusted amount of solvent would be necessary.

SUMMARY

An object of the present invention is to further develop a dosing device with an integrated balance to the effect that a defined formulation can be corrected on the basis of the local and promptly determined ambient parameters.

The object, according to one formulation, is achieved with a dosing device, with which liquid and/or solid substances can be combined in a specified mixing ratio with high accuracy. Such dosing device includes a balance, which comprises a weighing chamber; a processor; a climate module, which includes an air pressure sensor, an air humidity sensor and an air temperature sensor and which is disposed in the weighing chamber such that it can be removed; a data transmission path, over which data can be exchanged between the climate module and the processor; and comprising a formulation display. The invention makes use of the idea of using the climate module to detect directly in the dosing device the climate parameters that have an effect on the proportioning or, more specifically, the dosing of the substances that are to be combined. Then it is possible to suitably correct the applied formulation as a function of the climate parameters that are detected. As a result, it is possible to compensate, on the one hand, for the effects of ambient conditions on the dosing process as such, for example, the temperature-related variances in the volume-based dosing operation. It is also possible to compensate for the effects of the ambient conditions on the weighing result, determined by the balance, for example, the temperature-related measurement errors. On the whole, it can be ensured in this way that a defined formulation is observed with a much higher degree of accuracy.

According to one embodiment, it is provided that the climate module is connected to the processor via an electrical plug-in connection. The plug-in connection can be integrated into a mechanical receptacle, which is used to attach the climate module to the precision balance. In this way the data transmission path to the processor is automatically established, when the climate module is installed inside the draft shield. According to an alternative embodiment, it is provided that the climate module is coupled wirelessly to the processor. In this case the climate module can be disposed at any location inside the draft shield or the chassis of the balance, for example, on a side wall, where it will interfere the least, without having to take into consideration whether a plug-in connection can be arranged at this location in such a way that it is useful. In addition, the absence of a plug-in connection has the advantageous effect that the interior of the weighing compartment can be designed to be smoother and, therefore, easier to clean.

According to a preferred embodiment of the invention, it is provided that the balance is a precision balance, which has a draft shield that surrounds the weighing chamber. This embodiment is especially appropriate, if the objective is to combine very small amounts with very high precision, for example, with an accuracy in the range of milligrams or micrograms.

According to an additional embodiment of the invention, the balance is in a weighing compartment having a defined volume. In this case the balance does not have a separate draft shield. This embodiment is suitable for processing mixing orders in the paint mixing sector. Examples include repeat orders of paint for repairing damage to motor vehicles, caused, for example, by rocks or gravel or other road debris, in which case only very small amounts are used. These minimal amounts are produced based on the original formulation, where in this case it is possible to take into consideration the degree of aging that the complementary paint actually exhibits in each individual formulation that is to be applied.

The particular advantage of this embodiment consists of the feature that all of the components and functions, which are necessary for compensating for the climate changes in the weighing values, are combined in the dosing device comprising the precision balance. Therefore, no external computers, sensors, etc. are necessary. Instead, the user can be provided with a compact dosing device, which can be designed in such a way that it is even portable. Since the climate module is interchangeable (i.e., can be detached from the balance without destroying it), it can be sent, if desired, to an external institute or service provider for calibration. In the meantime the dosing device can still be used by installing a replacement climate module. As a result, it is possible to have on a rolling basis one or (in the case of several dosing devices) a plurality of climate modules being calibrated, while measuring with the other climate modules.

With respect to accuracy the inventive dosing device comprising the precision balance has the advantage that the climate parameters can be measured in the draft shield or in a weighing compartment immediately surrounding the balance. As a result, it is possible to determine the rate of evaporation directly at the weighing location and to provide a corresponding correction factor.

Preferably the climate module includes an air pressure sensor, an air humidity sensor and an air temperature sensor. These sensors can be used to record the climate data that are essential for a precise measurement.

According to one embodiment, a dosing device is provided that can be controlled electronically. This design allows the mixing process to be automated, so that the operator does not have to weigh each of the substances to be combined individually. As a result, this design avoids error sources that are the result of the manual intervention of an operator.

According to a further development, a treatment device can be provided, with which at least one of the substances to be combined can be treated, for example, can be heated or cooled. With respect to an optimal result, i.e., in particular, with respect to adhering to the defined formulation as precisely as possible, this embodiment permits the substances to be combined to be conditioned, since the density, the viscosity, etc. at the time of the dosing operation affect the dosing accuracy. The conditioning ensures that the physical properties of the substances to be combined correspond to those physical properties, on which the preparation of the formulation was based.

According to one embodiment, the climate module has an electronic memory, in particular, an EEPROM, which can be read out from the outside and in which the calibration values and the correction values for the climate module can be stored. In order to make adjustments, the calibration values and the correction values can be stored in an electronic memory on the climate module, in particular, can be stored in an EEPROM. This can be done at an external service provider. If the climate module is then reconnected to the precision balance, these data are then immediately available to the processor of the balance. In addition, the memory can be used to store, among other things, at least some of the following sensor calibration data: the number of the calibration certificate, the current calibration values, the calibration date, the name of the calibration laboratory, the name of the person in charge and the calibration history. In addition, so-called uncertainty values can also be stored for each climate variable in the memory of the climate module, so that they are available to compute the entire uncertainty of the measurement result, which are then available for output in a protocol.

According to one embodiment, it is provided that the climate module can also be used as a stand-alone unit external to a balance and can be connected to a USB port of a PC via an $I^2C$ bus. This arrangement makes it easier to perform an external calibration. In addition, the climate module can be used in other applications to record climate variables without having to be connected to a balance. For this purpose the printed circuit board of the climate module can easily have a plug-in extension, in order to be connected to a USB adapter.

The aforementioned object according to a further formulation is achieved with a method for dosing a formulation, using a dosing device of the type described above. In this case during dosage of the substances to be combined, ambient conditions are detected, and the mixing ratio of a formulation is either directly or indirectly adjusted in accordance with the ambient conditions. For this purpose the individually detected climate parameters, in particular, the air temperature, the air pressure and the air humidity are used to determine the correction factors for the individual constituents of the formulation, where the correction factors are extracted from a database. This database can be stored either directly in a memory of the balance or can be at an external storage location (for example, a database server), to which the balance is connected wirelessly or via a data line. With respect to the resulting higher accuracy of the dosing process, reference is made to the explanations above.

According to one embodiment of the method according to the invention, it is provided that the parameters of the ambient conditions are used to correct the weighing result of one of the substances to be combined. This embodiment compensates for the direct effect that the climate parameters have on the weighing result, i.e., for example, the effect of the changing ambient parameters on the behavior of the load cell or the effect of the varying high air pressure on the buoyancy of the sample to be weighed.

According to an additional embodiment of the method according to the invention, it is provided that the parameters of the ambient conditions are used to correct a dosing parameter of the substances to be combined. The ambient conditions also affect, in particular, the degree of accuracy, with which the substances to be combined can be weighed out. Temperature changes can lead to a change in the viscosity of the substances to be weighed out. Temperature changes also lead to a different density, a feature that affects a volume-based dosing in varying quantities. Finally it is also possible to compensate for the direct effect of the ambient conditions on the dosing system.

According to one variant of the method according to the invention, it is provided that the ambient conditions are used to pretreat at least one of the substances to be combined, prior to their being combined. For example, the substance to be treated can be heated or cooled, so that it is ensured that the physical properties of the substance to be weighed out are within a specified tolerance range. Similarly the moisture content of the substance to be weighed out can be adjusted in the desired manner, in order to obtain an optimal dosing result. Moreover, the parameters, ambient humidity and temperature, can be used to determine the dew point, which specifies a minimum temperature for the constituents of the formulation, in order to avoid unwanted condensation effects on the constituents of the formulation. Finally it can be provided that the formulation is adjusted to the subsequent conditions, under which the combined substances will be used. In this case the applied formulation is modified based on information that characterizes in more detail the subsequent conditions, under which the combined substances will be used. For the example of a paint it is possible to specify, for example, whether this paint shall be applied later under high or low temperatures or at a rather high humidity or rather low humidity. Then the solvent content, etc. can be adjusted in accordance with the conditions during application of the paint in such a way that the desired viscosity and the desired drying characteristics are ensured at a later point in the processing time. Similarly an integrated time measurement can be used to correct an evaporation process that has already started by adjusting the formulation, as a function of the known evaporation rates, the measured duration of the mixing process and the knowledge of the processing time.

BRIEF DESCRIPTION OF THE DRAWINGS

Additional features and advantages of the invention will become apparent from the following description and from the following drawings, to which reference is made. The drawings show in.

DETAILED DESCRIPTION

Figure 1:
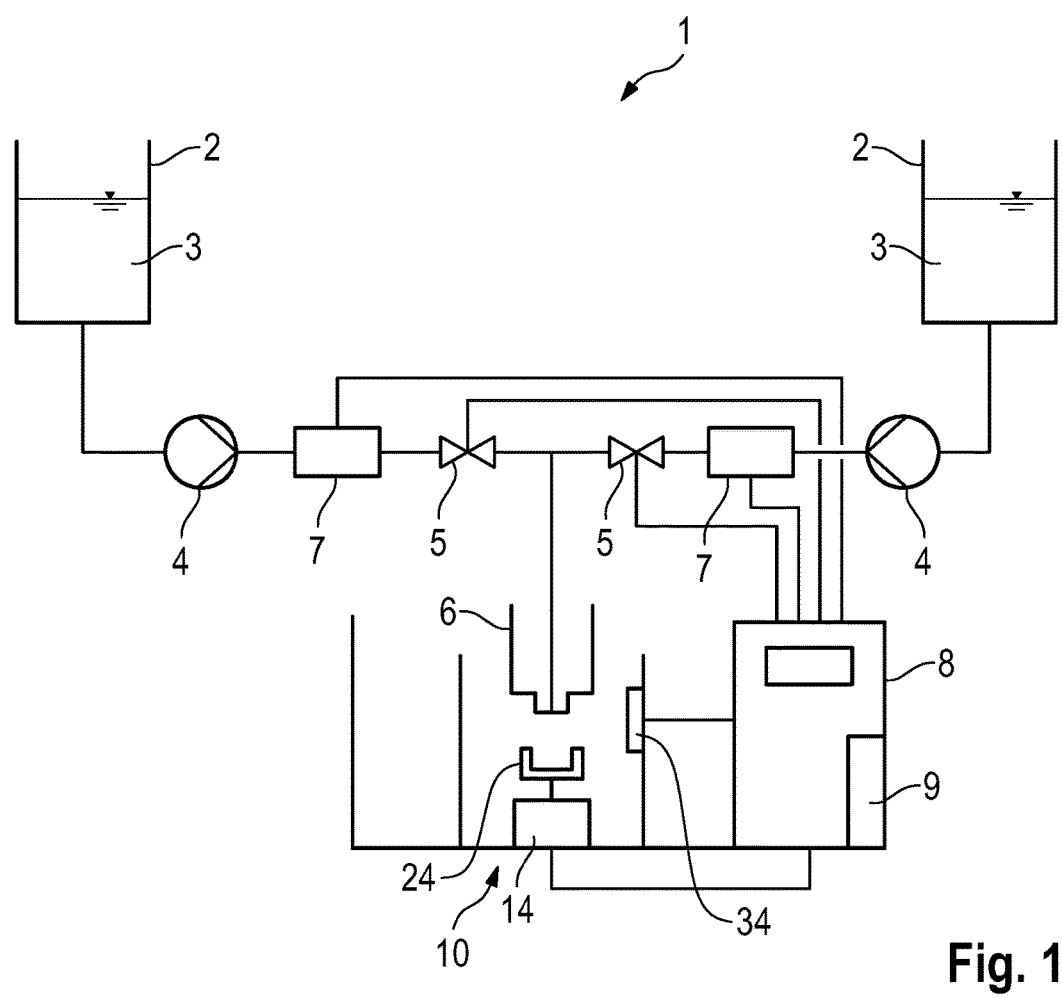
FIG. 1 in schematic form a view of a dosing device, according to the invention.

FIG. 1 shows in schematic form a dosing device 1, which comprises two storage vessels 2, in which the substances 3, for example, liquid or solid substances, to be mixed, are found. In the event that a paint is mixed, the substances can be, for example, color pigments, fillers and solvents.

The substances 3 can be conveyed by the pumps 4 and the dosing valves 5 from the storage vessels 2 to a dosing head 6. Optionally treatment devices 7 can be provided, for example, cooling systems or heating systems, with which the substances 3 can be treated. The treatment devices can also be drying or wetting devices.

Even though two storage vessels with two substances 3 are provided in the exemplary embodiment that is depicted, it goes without saying that, in principle, any number of different substances can be combined with the dosing device according to the invention.

Furthermore, the dosing device 1 includes a control unit 8, which can actuate the various components of the dosing device (for example, the pumps 4 and the dosing valves 5).

In the control unit 8, a formulation, i.e., the mixing ratio for the substances 3 to be combined, is also stored in a memory 9.

In addition, part of the dosing device 1 is a balance 10 that comprises a weighing dish 24 and a load cell 14. The weighing dish 24 is arranged in such a way that the combined substances 3 are placed on the weighing dish, so that the weight of the object can be determined by the load cell 14. The weight of the object is made available to the control unit 8.

An essential part of the dosing device 1 is a climate module 34, which is disposed in the vicinity of the balance 10, where the climate module detects the various climate parameters, in particular, the temperature, the air pressure and the humidity. These values are also made available to the control unit 8.

The control unit 8 is able to adjust, on the basis of the data of the climate module 34, a formulation, which is stored in the climate module, in such a way that it is possible to compensate for the effects of the micro climate in the dosing device 1 on the current mixing process in the best possible way.

Suitable correction tables, with the aid of which it is possible to correct the dosing parameters and the weighing result of the balance 10, are stored in the control unit 8.

If the dosing device 1 is used to mix high precision formulations, then a precision balance is used as a balance 10. An example of such a balance is shown in FIGS. 2 to 5. For the sake of a better overview and clarity, these figures do not show the other components of the dosing device, i.e., for example, the dosing head and the storage vessels.

Figure 2:
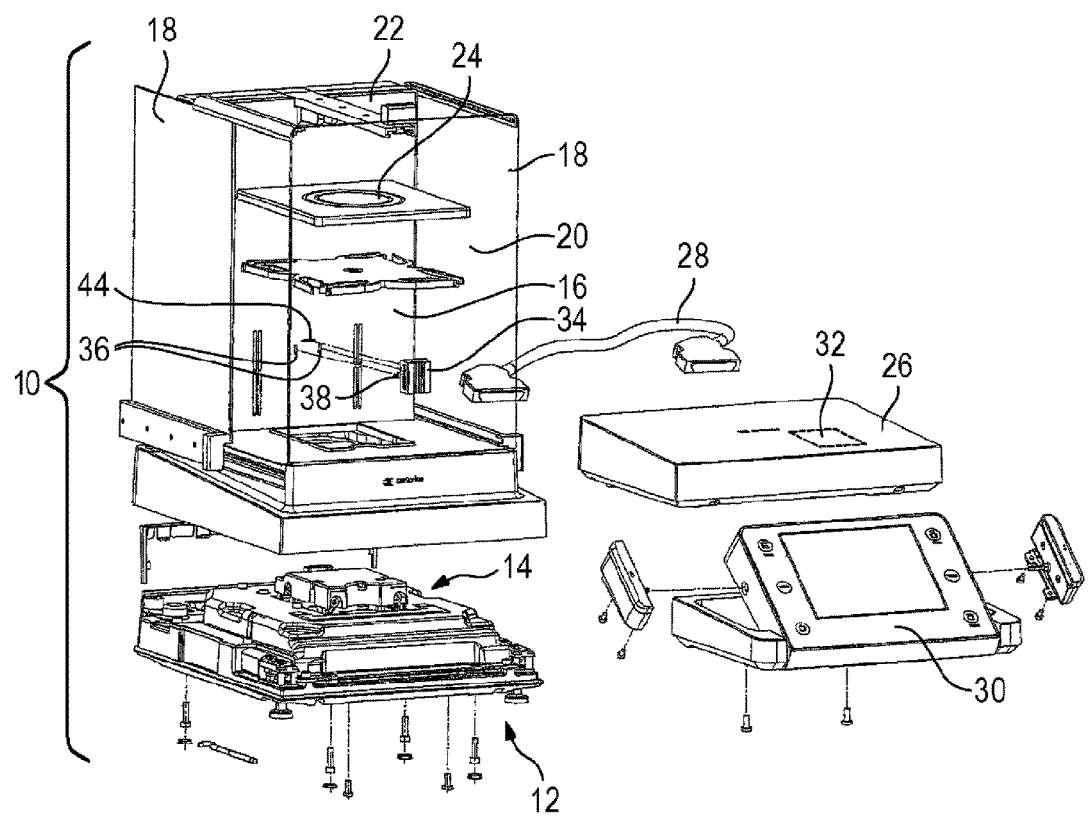
FIG. 2 an exploded view of a precision balance, which can be used in a dosing device according to the invention, FIG. 3 a perspective view of an inventive climate module, which can be used in the precision balance, shown in FIG. 2, FIG. 4 a side view of the climate module from FIG. 3 without the outer housing.

FIG. 2 shows a high resolution electronic balance (precision balance). This electronic balance includes a load cell 14 with a base 12. In addition, the balance 10 comprises a weighing chamber 16, which is formed by a draft shield with adjustable side walls 18, a front wall 20 and a rear wall 22. The draft shield separates the weighing chamber 16 from the surrounding area. A weighing dish 24 is used to hold the sample to be weighed, i.e., the substances 3 to be combined. These components together form a balance 10.

An electronic evaluation system 26, which is designed as a separate part in this embodiment, is electronically coupled to the load cell 14 via a cable 28. A display unit 30, which is coupled to the evaluation system 26, is used both as a display unit and as a data input unit. While the electronic evaluation system 26 and the display 30 are embodied as components physically separated from the balance 10 in the illustrated embodiment, other embodiments can incorporate one or both of these components 26 and 30 into the balance 10.

The display unit 30 is used as a mixing formulation display, on which a formulation to be prepared is displayed, in particular, the individual substances in the sequence and amounts, in which they are to be weighed out by the operator.

The electronic evaluation system 26 houses, among other things, a processor 32, which receives data from the load cell 14.

The weighing chamber 16 has a climate module 34, which is designed as a structurally separate unit and which can be mechanically coupled to the rear wall 22 via of a disconnectable plug-in connection (hence, is attached in a manner allowing the climate module to be disconnected without destroying it), and, in particular, preferably without the aid of a tool.

For this purpose the rear wall 22 has two slots 36, which are spaced apart from each other and in which flexible locking hooks 38 (see also FIG. 2) engage with the outer housing 40 of the climate module.

Figure 3:
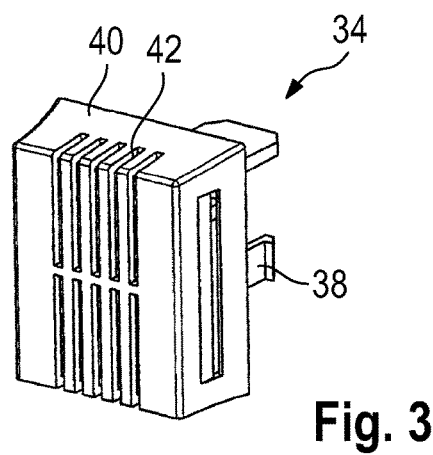
Figure 4:
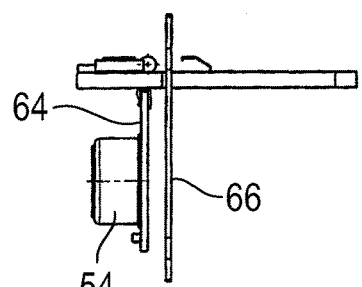
Figure 5:
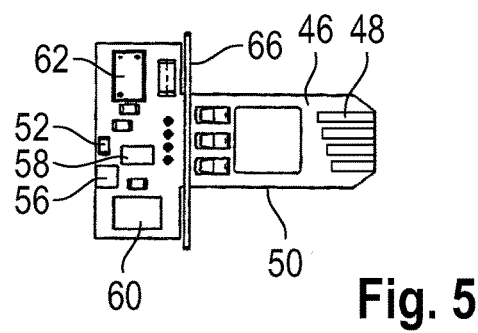
FIG. 5 a plan view of the climate module from FIG. 3, also without the outer housing.

FIGS. 3 to 5 show the climate module 34 in greater detail.

The outer housing 40 has a number of apertures 42, through which the interior of the outer housing 40 changes over into the weighing chamber 16 and becomes a part of the weighing chamber 16, so that the climate inside the weighing chamber 16 corresponds to the climate inside the outer housing 40.

The climate module 34 is electronically coupled via an electrical plug-in connection to a corresponding plug receptacle 44 in the rear wall 22. The plug receptacle 44 is electrically connected to the processor 32. A plug 46 with contacts 48 is plugged into the plug receptacle 44 on the climate module 34. As a result, the plug 46 forms a module-sided part of the electrical plug-in connection.

As an alternative to an electrical plug-in connection, a wireless type of transmission, such as WLAN or Bluetooth, can be used.

The electrical plug-in connection (or the wireless transmission used as an alternative) forms a data transmission path, over which the data can be transferred from the climate module 34 to the processor 32 and, if desired, can be transferred back to the climate module.

The plug 46 is preferably a section of a circuit board 50, on which a plurality of sensors for detecting the climate in the weighing chamber 16 are disposed. Therefore, an air temperature sensor 52, an air humidity sensor 54, a light sensor 56, which is arranged in the immediate vicinity of an aperture 42, and, optionally, other sensors 58 are provided on the circuit board 50, and an electronic memory 60 is also provided on the circuit board. An air pressure sensor 62 is mechanically and electrically coupled to the circuit board 50 via a bracket 64.

A plurality of the sensors can also be combined into combined sensors.

A wall 66 closes the shell-like outer housing 40, so that the narrow tongue-like section of the circuit board 50, which is located to the right of the wall 66 in FIG. 4, can be inserted into the rear wall 22 and the plug receptacle 44.

Each sensor is coupled to the processor 32 via corresponding contacts 48. Similarly the memory 60 is coupled to the processor 32.

In a weighing process the density of the sample to be weighed can be entered into the precision balance, for example, via the display unit 30, which is also used simultaneously as a data input unit. As an alternative, the density of the sample to be weighed can have already been stored.

Then a sample to be weighed is placed on the weighing dish 24, i.e., a defined amount of substance according to the formulation.

The air pressure, the air humidity and the air temperature are determined by the sensors 62, 54 and 52, respectively; and the corresponding data are then transmitted to the processor 32.

The processor 32 processes the individual climate parameters and determines, for example, the rate of evaporation, from which the correction factors for the individual constituents of the formula are determined.

In addition, the calibration values and the correction values for the climate module 34, which had been input during the calibration of the climate module 34, are stored in the memory 60

This calibration is performed outside of the precision balance. To this end the climate module 34 is simply removed from the weighing chamber 16 without having to disconnect a wire connection. Then the climate module 34 is sent to an appropriate calibration institute that recalibrates the sensor accordingly and stores, for example, the number of the calibration certificate, the calibration date, the name of the calibration laboratory, the name of the person in charge and the calibration history in the memory 60. The calibration values, which have been determined anew, are read out later by the application program, when the climate module 34 is once again in the precision balance, and flow directly into the computation.

Even the values of the light sensor 56 and, optionally, other sensors 58 are determined.

For example, when the level of incident light increases, a corresponding signal will be shown on the display that, for example, the measurement is uncertain due to increased exposure to sunlight and, thus, due to a temperature change in the weighing chamber. As a result, the processor outputs an output signal as a function of the exposure to incident light.

The memory 60 is preferably an EEPROM.

The connection between the climate module 34 and the precision balance can be implemented via an $I^2C$ bus.

The climate module 34 can be connected to a computer via a USB adapter, into which the climate module is inserted, in order to calibrate the sensors 52 to 58 and 62 without having to connect the climate module 34 to the balance 10.

As can be seen, the climate module is designed in such a way that it can also be used as a stand-alone unit external to a balance and can be connected, for example, to a PC via an $I^2C$ bus.

A precision balance of this type can be used to adhere to the mixing ratios or, more specifically, to the formulations with extremely high accuracy, where in this case it is possible to compensate for the potential effect factors, which are due to the micro climate in the area of the dosing device and, in particular, in the area of the balance 10.

LIST OF REFERENCE NUMERALS 1 dosing device
2 storage vessel
3 substance
4 pump
5 dosing valve
6 dosing head
7 treatment device
8 control unit
9 memory
10 balance
12 base
14 load cell
16 weighing chamber
18 side wall
20 front wall
22 rear wall
24 weighing dish
26 evaluation system
28 cable
30 display unit
32 processor
34 climate module
36 slots
38 locking hooks
40 outer housing
42 apertures
44 plug receptacle
46 plug
48 contacts
50 printed circuit board
52 air temperature sensor 54 air humidity sensor
56 light sensor
58 sensor
60 memory
62 air pressure sensor
64 bracket
66 wall

What is claimed is:

1. Dosing device comprising:
a source for at least two segregated substances;
a dosing arrangement configured to combine the substances in a defined mixing ratio;
a balance, which comprises a weighing chamber, a processor, and a climate module, which includes an air pressure sensor, an air humidity sensor and an air temperature sensor, which outputs climate data, and which is detachably disposed in the weighing chamber;
a data transmission path, over which data is exchanged between the climate module and the processor; and
a control unit configured to control the dosing arrangement to adjust the defined mixing ratio in accordance with the climate data from the climate module.

2. The dosing device as claimed in claim 1, wherein the data transmission path comprises an electrical plug-in connection or a wireless transmission path.

3. The dosing device as claimed in claim 1, wherein the balance is a precision balance and wherein the weighing chamber is delimited by a draft shield.

4. The dosing device as claimed in claim 1, wherein the weighing chamber comprises a light sensor, which is coupled to the data transmission path.

5. The dosing device as claimed in claim 1, wherein the control unit controls the dosing arrangement electronically.

6. The dosing device as claimed in claim 1, further comprising a treatment device configured to treat at least one of the substances to be combined.

7. The dosing device as claimed in claim 1, wherein
the climate module further comprises a self-contained modular unit comprising the air pressure sensor, the air humidity sensor and the air temperature sensor,
the data transmission path is configured to transmit data from the modular unit to the processor, which is external to the climate module, and
wherein the dosing device further comprises a mounting mechanism configured to secure the climate module detachably to a further component of the dosing device.

8. The dosing device as claimed in claim 7, wherein the climate module further comprises an electronic memory configured to store calibration values and correction values for the climate module in a form readable by a reader of an electronic system that is external to the climate module.

9. The dosing device as claimed in claim 7, wherein the climate module is configured as a stand-alone unit external to the dosing device and configured to connect to a computer.

10. Method for mixing a formulation using a dosing device as claimed in claim 1, comprising:
detecting ambient conditions within the dosing device during dosage of substances to be combined by the dosing device, and
adjusting a mixing ratio of the substances to be combined in accordance with the detected ambient conditions.

11. The method as claimed in claim 10, further comprising correcting a dosing parameter of the substances to be combined in accordance with the detected ambient conditions.

12. The method as claimed in claim 10, further comprising treating at least one of the substances to be combined prior to the substances being combined, in accordance with the detected ambient conditions, wherein the treating consists essentially of: heating, cooling, wetting and/or drying at least one of the substances.

13. The method as claimed in claim 10, further comprising:
combining the substances at the adjusted mixing ratio, and
further adjusting the mixing ratio to application conditions of the substances subsequent to the substances being combined.

* * * * *